United States Patent
Wright et al.

(10) Patent No.: US 9,155,621 B2
(45) Date of Patent: *Oct. 13, 2015

(54) ANNULOPLASTY RING HOLDER

(75) Inventors: John T. M. Wright, Denver, CO (US); Hieu Cong Nguyen, Denver, CO (US)

(73) Assignee: Medtronic, Inc., Minneapolis, MN (US)

(*) Notice: Subject to any disclaimer, the term of this patent is extended or adjusted under 35 U.S.C. 154(b) by 3 days.

This patent is subject to a terminal disclaimer.

(21) Appl. No.: 13/453,583

(22) Filed: Apr. 23, 2012

(65) Prior Publication Data

US 2012/0215302 A1  Aug. 23, 2012

Related U.S. Application Data

(63) Continuation of application No. 12/721,019, filed on Mar. 10, 2010, now Pat. No. 8,163,009, which is a continuation of application No. 11/534,188, filed on Sep. 21, 2006, now Pat. No. 7,691,143.

(60) Provisional application No. 60/719,483, filed on Sep. 21, 2005.

(51) Int. Cl.
A61F 2/24  (2006.01)

(52) U.S. Cl.
CPC ............ *A61F 2/2445* (2013.01); *A61F 2/2466* (2013.01)

(58) Field of Classification Search
USPC .................................. 623/2.1–2.38
See application file for complete search history.

(56) References Cited

U.S. PATENT DOCUMENTS

| | | | |
|---|---|---|---|
| 3,983,581 A | 10/1976 | Angell et al. | |
| 4,042,979 A | 8/1977 | Angell et al. | |
| 4,106,129 A | 8/1978 | Carpentier et al. | |
| 4,451,936 A | 6/1984 | Carpentier et al. | |
| 4,865,600 A | 9/1989 | Carpentier et al. | |
| 5,011,481 A | 4/1991 | Myers et al. | |
| 5,032,128 A | 7/1991 | Alonso | |
| 5,041,130 A | 8/1991 | Cosgrove | |
| 5,290,300 A | 3/1994 | Cosgrove | |
| 5,350,420 A * | 9/1994 | Cosgrove et al. | 623/2.11 |
| 5,496,336 A | 3/1996 | Cosgrove | |
| 5,522,884 A | 6/1996 | Wright | |

(Continued)

FOREIGN PATENT DOCUMENTS

GB  2108393  5/1983

OTHER PUBLICATIONS

Abe et al. (1990 "Left Ventricular Rupture Following Mitral Valve Surgery" Rinsho Kyobu Geka 10(1):72-75: Abstract Only.

(Continued)

*Primary Examiner* — Suzette J Gherbi

(57) ABSTRACT

An annuloplasty ring holder including a head having an upper surface and an annuloplasty ring receiving surface facing opposite the upper surface. The annuloplasty ring holder also includes means for attaching an annuloplasty ring to the annuloplasty ring receiving surface. The means for attaching an annuloplasty ring to the annuloplasty ring receiving surface may include one or more suture guides operatively associated with the head and configured to position one or more sutures to removably associate an annuloplasty ring with the annuloplasty ring receiving surface. The head may include a central hub and more than one spoke radiating out from the central hub. If the head is thus configured, each spoke will include a portion of the annuloplasty ring receiving surface.

6 Claims, 7 Drawing Sheets

(56) References Cited

U.S. PATENT DOCUMENTS

| | | | |
|---|---|---|---|
| 5,669,919 | A | 9/1997 | Sanders et al. |
| 5,683,402 | A | 11/1997 | Cosgrove |
| 5,843,177 | A | 12/1998 | Vanney et al. |
| 5,843,178 | A | 12/1998 | Vanney et al. |
| 5,972,030 | A | 10/1999 | Garrison et al. |
| 6,001,127 | A | 12/1999 | Schoon et al. |
| 6,004,329 | A | 12/1999 | Myers et al. |
| 6,136,017 | A | 10/2000 | Craver et al. |
| 6,197,053 | B1 | 3/2001 | Cosgrove et al. |
| 6,283,993 | B1 | 9/2001 | Cosgrove |
| 6,319,280 | B1 | 11/2001 | Schoon |
| 6,406,492 | B1 | 6/2002 | Lytle |
| 6,558,416 | B2 | 5/2003 | Cosgrove |
| 6,749,630 | B2 | 6/2004 | McCarthy |
| 6,802,860 | B2 | 10/2004 | Cosgrove |
| 7,377,940 | B2 | 5/2008 | Ryan et al. |
| 7,476,247 | B2 | 1/2009 | Ryan et al. |
| 7,575,595 | B2 | 8/2009 | Ingle et al. |
| 7,691,143 | B2 * | 4/2010 | Wright et al. ............... 623/2.11 |
| 8,048,255 | B2 * | 11/2011 | Wright ....................... 156/304.6 |
| 8,163,009 | B2 * | 4/2012 | Wright et al. ............... 623/2.11 |
| 2003/0144732 | A1 * | 7/2003 | Cosgrove et al. ........... 623/2.11 |
| 2005/0027352 | A1 | 2/2005 | Cosgrove |
| 2005/0182487 | A1 | 8/2005 | McCarthy et al. |
| 2006/0025856 | A1 | 2/2006 | Ryan et al. |
| 2006/0217803 | A1 * | 9/2006 | Ingle et al. .................. 623/2.11 |
| 2007/0078514 | A1 | 4/2007 | Ryan et al. |
| 2007/0299513 | A1 | 12/2007 | Ryan et al. |
| 2008/0183284 | A1 | 7/2008 | Ryan et al. |
| 2009/0299470 | A1 | 12/2009 | Rao et al. |
| 2011/0066236 | A1 | 3/2011 | Khalapyan |

OTHER PUBLICATIONS

American Edwards Laboratories Instructions for Use for the "Carpentier-Edwards Model 2625 (aortic) and Models 6625 and 6625-ESR" (mitral) Bioprostheses [Glutaraldehyde-Preserved Flexible Support-Mounted Porcine Valves] (Oct. 1996).
Anderson and Wilcox (1995) "Understanding Cardiac Anatomy: The Prerequisite for Optimal Cardiac Surgery" Ann Thorac. Surg., 59:1366-75.
Carpentier (1982) "Continuing Improvements in Valvular Bioprostheses" J. Thorac Cardiovasc Surg 83:27-42.
Davila (1976) letter to the editor: Ann Thorac Surg., 22(2):207-08.
Duran (2000) "Druan Flexible Annuloplasty: Repair of the Mitral and Tricuspid Valves—Indications, Patient Selection, and Surgical Techniques Using the Duran Flexible Annuloplasty Ring" Medtronic, Inc. manual pp. 1-62.
Garcia-Rinaldi et al. "Conservative Repair of Mitral and Tricuspid Valves" (Jan. 17, 2001) Cardiovascular Surgery of Texas; Memorial Hospital, Houston, Texas; Centro Medico Nacional Valdecilla, Santander, Spain; copyright Baylor College of Medicine; 14 pages.
Hufnagel (1959) "Direct Approaches for the Treatment of Aortic Insufficiency" American Surgeon, 25:321-327.
Hufnagel et al. (1966) "Cardiac Valve Replacement—Its Current Status" Medical Annals of the District of Columbia, 35(9):357-62.
Hufnagel and Conrad (1968) "A New Approach to Aortic Valve Replacement" Annals of Surgery, 167(5):791-95.
Hufnagel (1979) "Basic Concepts in the Development of Cardiovascular Prostheses" Great Ideas in Surgery, 137:285-300.
Meyer and Bircks (1977) "Predictable Correction of Tricuspid Insufficiency by Semicircular Annuloplasty" Ann Thorac Surg., 23:574-575.
Spampinato andlorio (1981) "Entanglements of Sutures with Struts of Mitral Bioprosthesis: How to Prevent It" Ann Thorac Surg., 31(5):478-79.
Stefanik et al. (1976) "A Method for Insertion of a Stented Xenograft Valve in the Artioventricular Position" Ann Thorac Surg., 21(2):166-7.
Wright et al. (1982) "Hancock II—An Improved Bioprosthesis" (Hancock/Extracorporeal 1982), pp. 425-438.
Wright et al. (1982) "Hancock II—Status Report" The Department of Valvular Research, Extracorporeal, Inc., pp. 189-200.
Zimmerman (1966) "Functional and Surgical Anatomy of the Heart", Royal College of Surgeons of England, 39(6):348-66.
International Search Report and Written Opinion for corresponding International Application No. PCT/US2006/36851 filed Sep. 21, 2006.
Inter Partes Reexamination Request for U.S. Pat. No. 7,691,143, Control No. 95/000,694, submitted Sep. 13, 2012.
Order Granting Reexamination and Non-Final Office Action issued in Reexamination of U.S. Pat. No. 7,691,143, Control No. 95/000,694, issued Jun. 17, 2013.
Patent Owner's Response to Office Action filed in Reexamination of U.S. Pat. No. 7,691,143, Control No. 95/000,694, submitted Aug. 19, 2013.
Action Closing Prosecution issued in Reexamination of U.S. Pat. No. 7,691,143, Control No. 95/000,694, issued Oct. 23, 2013.
Patent Owner's Response to Action Closing Prosecution filed in Reexamination of U.S. Pat. No. 7,691,143, Control No. 95/000,694, submitted Nov. 25, 2013.
Right of Appeal Notice issued in Reexamination of U.S. Pat. No. 7,691,143, Control No. 95/000,694, issued Jan. 15, 2014.
Patent Owner's Brief on Appeal filed in Reexamination of U.S. Pat. No. 7,691,143, Control No. 95/000,694, submitted May 2, 2014.
Inter Partes Reexamination Request for U.S. Pat. No. 8,163,009, Control No. 95/000,693, submitted Sep. 13, 2012.
Order Granting Reexamination and Non-Final Office Action issued in Reexamination of U.S. Pat. No. 8,163,009, Control No. 95/000,693, issued Oct. 26, 2012.
Patent Owner's Response to Office Action filed in Reexamination of U.S. Pat. No. 8,163,009, Control No. 95/000,693, submitted Feb. 11, 2013.
Action Closing Prosecution issued in Reexamination of U.S. Pat. No. 8,163,009, Control No. 95/000,693, issued Apr. 16, 2013.
Patent Owner's Response to Action Closing Prosecution filed in Reexamination of U.S. Pat. No. 8,163,009, Control No. 95/000,693, submitted May 16, 2013.
Right of Appeal Notice issued in Reexamination of U.S. Pat. No. 8,163,009, Control No. 95/000,693, issued Sep. 11, 2013.
Notice of Intent to Issue Inter Partes Reexamination Certificate issued in Reexamination of U.S. Pat. No. 8,163,009, Control No. 95/000,693, issued Nov. 16, 2013.

* cited by examiner

ANNULOPLASTY RING HOLDER

RELATED APPLICATIONS

This application is a Continuation of U.S. patent application Ser. No. 12/721,019, filed Mar. 10, 2010, now U.S. Pat. No. 8,163,009, issued Apr. 24, 2012; which is a Continuation of U.S. patent application Ser. No. 11/534,188 filed Sep. 21, 2006, now U.S. Pat. No. 7,691,143, issued Apr. 6, 2010, which claims priority from U.S. Provisional Patent Application Ser. No. 60/719,483, filed Sep. 21, 2005, entitled Annuloplasty Ring Holder.

TECHNICAL FIELD

The present invention is directed toward an annuloplasty ring holder and more particularly toward an annuloplasty ring holder with an annuloplasty ring receiving surface facing opposite an upper surface.

BACKGROUND ART

Annuloplasty rings are used to stabilize and restrict the mitral or tricuspid annulus in heart valve repair surgery. There are several different types of annuloplasty rings in current clinical use. For example, the Carpentier-Edwards ring is a rigid "D" shaped semi-closed ring. The Cosgrove-Edwards band is a fully flexible "C" shaped ring, and the Medtronic-Duran ring is a fully flexible circular ring.

Annuloplasty ring holders are particularly useful for use during implantation of flexible annuloplasty rings because of certain surgical attachment and positioning challenges caused by the very nature of the rings' flexibility. Without a holder, the surgical assistant has to retain the ring using his or her fingers, or using a pair of forceps. This is awkward as the ring holding point has to be frequently readjusted as the several implantation sutures are placed through the circumference of the ring body. For this reason, many surgeons prefer that flexible annuloplasty rings be supplied mounted on disposable holders.

An annuloplasty ring is often secured to the holder using one or more sutures that may pass through the body of the ring or around a ring section. The ring is released from the holder by severing one or more of the retaining sutures.

Prior art annuloplasty ring holders feature a circumferential channel or flange against which the annuloplasty ring may be secured. Typically holders are substantially planar. Thus, with prior art devices the annuloplasty ring is positioned around the outer circumference of the planar holder structure. This configuration can in certain instances limit a surgeon's ability to securely abut an annuloplasty ring against a patient's annulus since the holder may interfere with proper positioning. In addition, prior art annuloplasty ring holders typically feature a holder head having a curved or shaped circumferential channel or flange which supports the ring along some or all of its inner circumference. Such devices excel at holding an annuloplasty ring in a desired shape. However the extended ring contact along a shaped circumferential supporting surface or channel can limit a surgeon's ability to effectively place attachment sutures through the ring. In particular, an extended ring contact surface prohibits a surgeon from using running sutures. Circumferential ring placement on a holder can also hinders efficient ring release after implantation. The present invention addresses one or more of these concerns.

SUMMARY OF THE INVENTION

The present invention is an annuloplasty ring holder including a head having an upper surface and an annuloplasty ring receiving surface facing opposite the upper surface. The annuloplasty ring holder also includes means for attaching an annuloplasty ring to the annuloplasty ring receiving surface. The means for attaching an annuloplasty ring to the annuloplasty ring receiving surface may include one or more suture guides operatively associated with the head and configured to position one or more sutures to removably associate an annuloplasty ring with the annuloplasty ring receiving surface.

The head of this embodiment may include a central hub and more than one spoke radiating out from the central hub. If the head is thus configured, each spoke will include a portion of the annuloplasty ring receiving surface. In a hub and spoke embodiment the means for attaching an annuloplasty ring to the annuloplasty ring receiving surface of any given spoke may include at least one suture guide operatively associated with the spoke and configured to position a suture for the removable association of an annuloplasty ring with that portion of the annuloplasty ring receiving surface on the spoke. The suture guide may include at least one hole passing through the select spoke between the upper surface and the portion of the annuloplasty ring receiving surface associated with the spoke. The suture guide may also include a groove operatively associated with a distal end of the select spoke the groove defining a channel for a suture to pass between the upper surface and the annuloplasty ring receiving surface.

The annuloplasty ring holder of this embodiment may include any number of spokes and the number and configuration of the spokes may be selected to hold annuloplasty rings of various configurations. An annuloplasty ring holder with five spokes may to be useful for supporting a partial or C-shaped flexible ring. Similarly an annuloplasty ring holder with six spokes may be used to support a complete ring.

The annuloplasty ring holder may include a circumferential suture channel around the hub and a handle extending from the upper surface. The handle may include a stem and an attachment member. In addition the head may include a central hole defined by the hub and configured to receive the attachment member, thus providing for a detachable handle. It is desirable that the stem be sufficiently malleable that it may be bent into a desired configuration in normal use. A particularly useful stem may be made of a shape memory metal which may be heat set in an initial straight or linear configuration prior to use, bent as desired during use, and which will return to the straight shape upon heat sterilization.

Another embodiment of the present invention is an annuloplasty ring and holder combination. The annuloplasty ring holder may be as is described above. In the combination embodiment an annuloplasty ring is removably associated with the annuloplasty ring receiving surface of the head. This embodiment may include a ring suture as the mechanism for removably associating the annuloplasty ring to the head. Preferably, a single ring suture which is also securely attached to the head is used to secure the ring. In addition, a retaining suture may be used to removably associate the ring suture with the central hub. Preferably the retaining suture is tied and configured such that severance of the retaining suture in one place will allow the ring suture to be fully released from the ring.

Another aspect of the present invention is a method of attaching an annuloplasty ring to an annuloplasty ring holder. The method includes providing an annuloplasty ring holder as described above and removably attaching an annuloplasty ring to the annuloplasty ring receiving surface. The ring may be attached with a ring suture, and the ring suture may be attached to the head with a retaining suture.

Another aspect of the present invention is a method of releasing an annuloplasty ring from an annuloplasty ring holder as described above. The method includes severing a retaining suture in a single place which allows the full disassociation of a ring suture from an implanted annuloplasty ring.

Another aspect of the present invention is a method of implanting an annuloplasty ring. The implantation method includes providing an annuloplasty ring holder and ring as described above. According to the implantation method a surgeon will place an implanting suture in the annulus of a patient and place the annuloplasty ring and holder near the patient's chest. The implanting suture may then be passed through the annuloplasty ring and the annuloplasty ring and holder may be pushed down the implanting suture so that the annuloplasty ring lies against the annulus. Implantation knots may then be tied in the implantation suture. Subsequently the retaining suture may be severed releasing the ring suture and allowing the removal of the ring suture from between the annuloplasty ring and annulus and subsequent removal of the annuloplasty ring holder.

DETAILED DESCRIPTION OF THE PREFERRED EMBODIMENT

Figure 1:
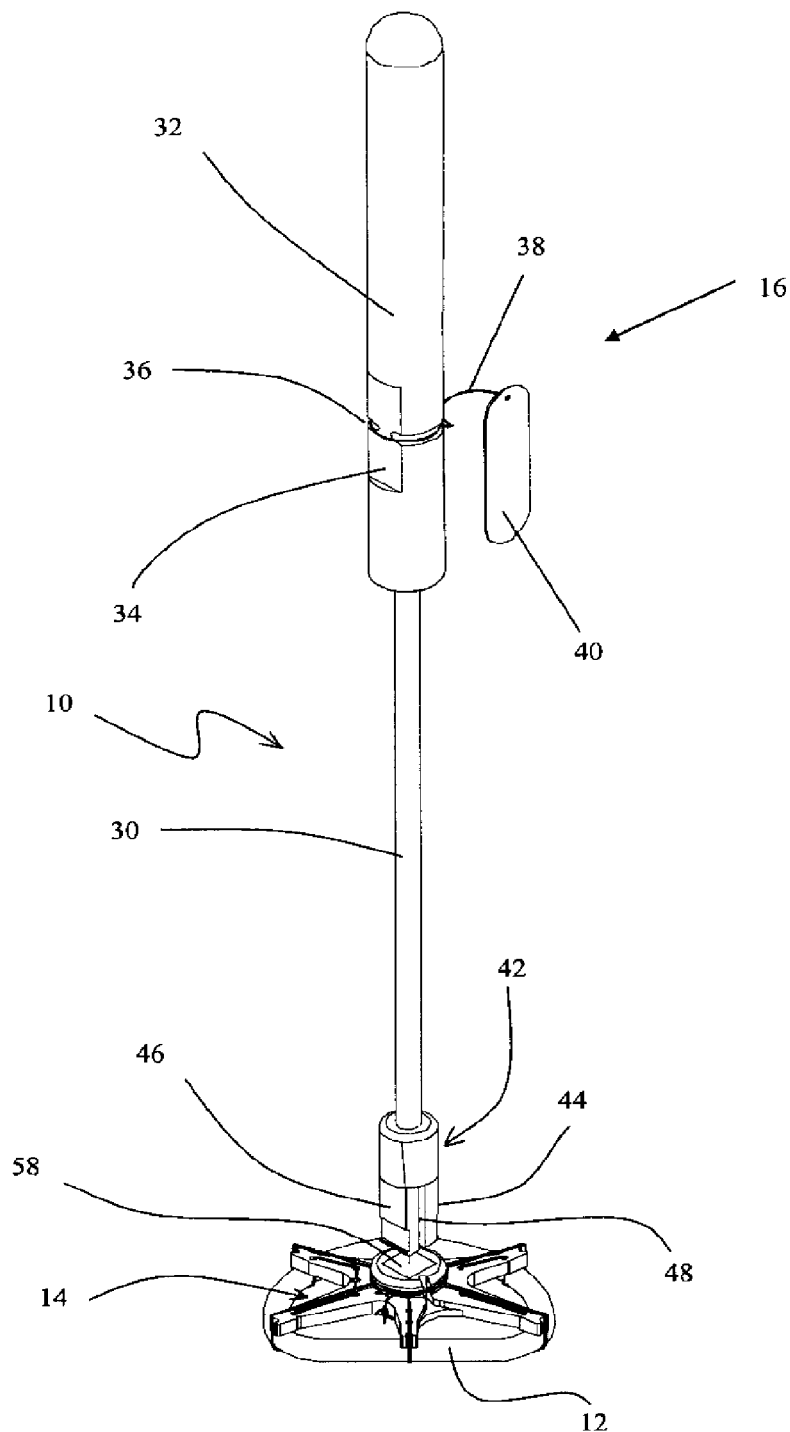
FIG. 1 is an isometric view of the holder with an annuloplasty ring attached. The holder handle and stem have been detached.

FIG. 1 is an isometric view of an annuloplasty ring holder 10 with an annuloplasty ring 12 attached. Although shown in FIG. 1 with a head 14 and a handle 16, the annuloplasty ring holder 10 of the present invention may be supplied as a head 14 only. Certain embodiments will include a handle 16, the invention is not however limited to such embodiments.

Figure 2:
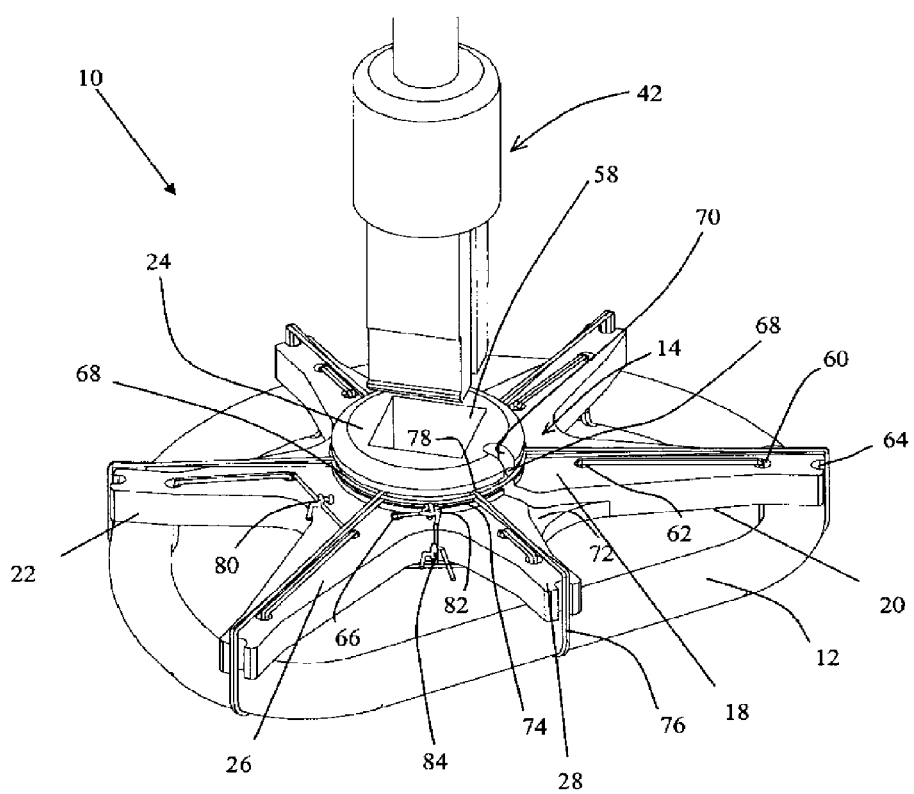
FIG. 2 is an isometric view of the holder with an annuloplasty ring attached. The releasable member at the base of the stem has been detached from the holder.

FIG. 2 is an isometric view of a holder 10 consistent with the present invention. The head 14 includes an upper surface 18 and an annuloplasty ring receiving surface 20 facing opposite the upper surface. The present invention is not limited to head 14 embodiments which are substantially planar, however in a planar implementation the upper surface 18 faces the handle 16 if a handle 16 is present. The annuloplasty ring receiving surface 20 is opposite the upper surface 18 and faces away from the handle 16. Positioned substantially between the upper surface 18 and the annuloplasty ring receiving surface 20 is a circumferential edge 22 which may be of any thickness. Removable association of an annuloplasty ring 12 with the annuloplasty ring receiving surface 20 of the present invention is a significant departure from prior art annuloplasty ring holders which rely upon the circumferential edge 22 to support the ring. The novel placement of an annuloplasty ring 11 against an annuloplasty ring receiving surface 20 opposite the upper surface 18 and handle 16 facilitates ring placement, provides for superior release of the annuloplasty ring from the holder after implantation and allows for the use of an open spoke design as is discussed in detail below. Such advantages are difficult or impossible to achieve with prior art embodiments where a ring is mounted in a circumferential groove, against a circumferential flange or otherwise associated with a circumferential edge.

As is shown in FIG. 2 the head 14 may include a central hub 24 and more than one spoke 26 radiating out from the central hub 24. In a spoke and hub embodiment each spoke 26 will include a portion of the annuloplasty ring receiving surface. Spokes 26 may be configured to point at or identify certain anatomical structures associated with a heart valve or annulus. Spokes also allow the use of running sutures if desired by the surgeon. The embodiment shown in the figures features six spokes of dissimilar length. A six spoke embodiment of the present invention is suitable for supporting a complete annuloplasty ring as shown in the figures. The dissimilar length of the spokes 26 provides for the ring to be held in a suitable shape when attached to the holder 10 for implantation. An embodiment with five spokes may be used with a partial or "C" shaped flexible ring. Other embodiments with different numbers, lengths or configurations of spokes 26 will be readably apparent to those skilled in the art.

The head 14 includes means for removably attaching an annuloplasty ring to the annuloplasty ring receiving surface 20. The means for attachment could be a mechanical structure, such as a clip or bracket or a chemical bond or weld such as an easily broken glue joint. A preferred embodiment of the present invention however will include one or more suture guides 28 associated with the head 14 and configured to position one or more sutures to removably associate an annuloplasty ring 12 with the annuloplasty ring receiving surface 20. As shown in FIG. 2 the suture guide 28 may include at least one hole passing through the head 14, between the upper surface 18 and the annuloplasty ring receiving surface 20. The suture guide 28 may also include a groove or other structure operatively associated with a distal end of a spoke 26 defining a channel for a suture to pass between the upper surface 18 and the annuloplasty ring receiving surface 20.

Referring back to FIG. 1 it is shown that the holder handle 16, if present, has a stem 30 which is preferably malleable, a grip 32 and two opposing flats 34 (only one flat 34 is visible in FIG. 1). The flats 34 may be used by the surgeon to properly orient the ring and holder 10 during surgery. A groove 36 associated with the handle 16 is used to retain a suture 38 that may hold a serial number or other identification identity tag 40. A malleable stem 30 is preferable since a surgeon may desire to bend the stem 30 in use for proper ring positioning. Similarly, a stem made of a shape memory alloy such as Nitinol or other nickel-titanium alloys is particularly advantageous. A shape memory stem 30 may be heat set in a straight configuration, bent as needed by a surgeon during use, and restored to its original straight configuration by reheating during subsequent sterilization processes.

Figure 3:
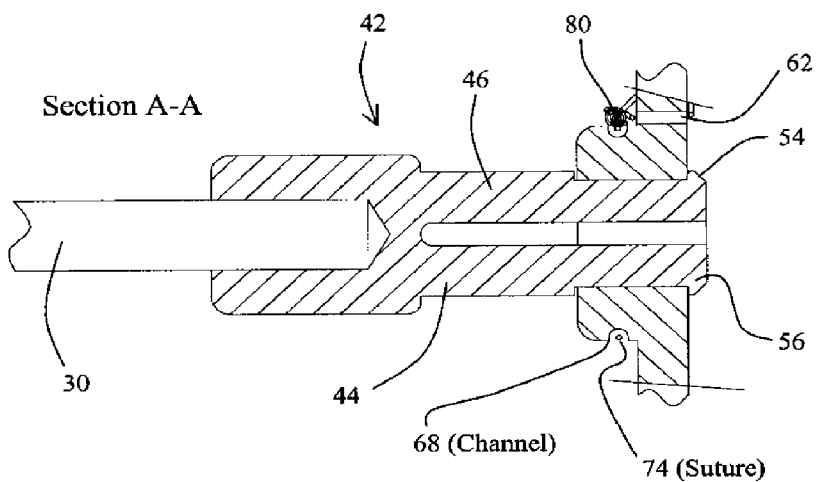
FIG. 3 is a partial cross sectional view of the holder hub and stem attachment member taken along line A-A of FIG. 2.
Figure 4:
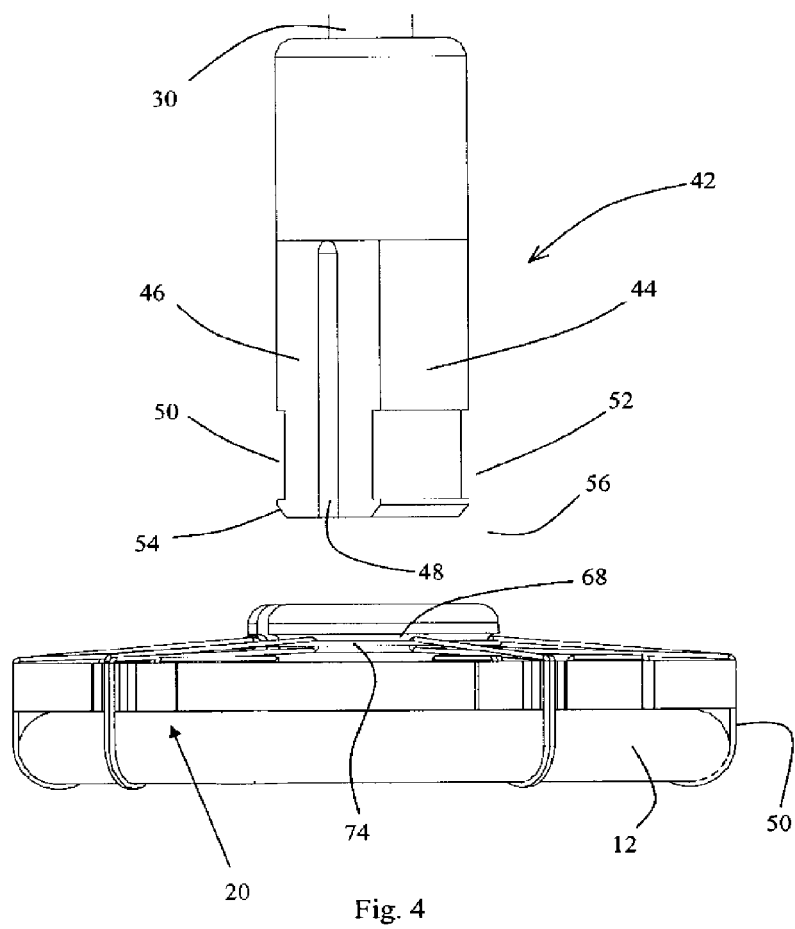
FIG. 4 is a side elevation view of the holder with an annuloplasty ring attached. The releasable member at the base of the stem has been detached from the holder.

The distal end of the malleable stem 30 may include an attachment member 42 that has two parallel leg members 44, 46 separated by slot 48. FIGS. 3 and 4 show a detailed view of the attachment member 42 and associated structures. Stepped portions 50, 52 are terminated with chamfered flanges 54, 56. When parallel leg members 44, 46 are squeezed together (by forceps applied close to steps 50, 52), parallel legs 44, 46 bend inward sufficiently to allow flanges 54, 56 to be freely inserted into a hole 58 in the head 14. Preferably, the hole 58 is polygonal to assure that the head 14 can not rotate with respect to the handle 16.

Figure 5:
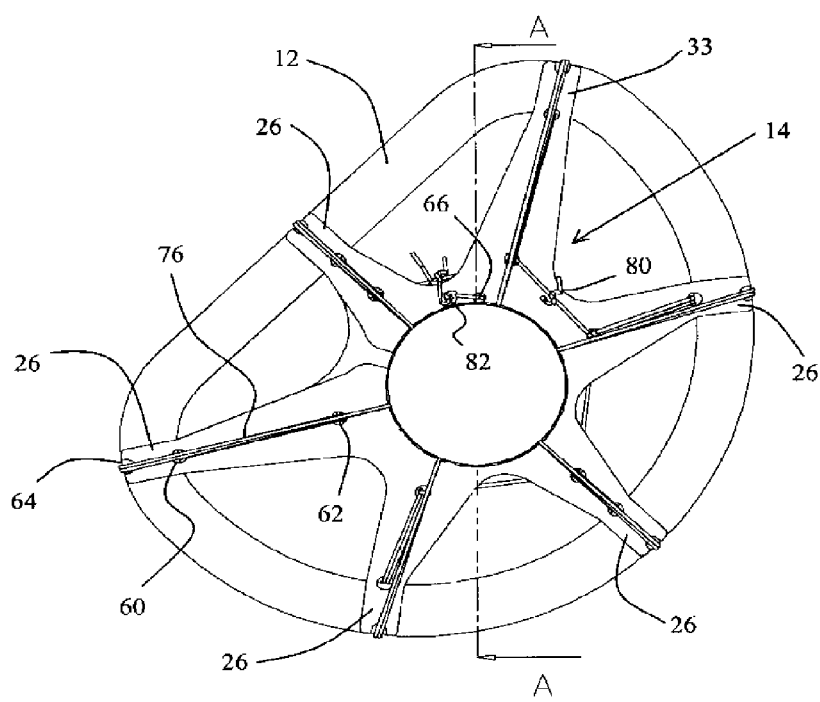
FIG. 5 is a plan view of the holder and handle with an annuloplasty ring attached.

One embodiment of the suture guide 28 described generally above is shown in detail on FIG. 2 and FIG. 5, a plan view of the head 14. In this embodiment, each spoke 26 contains an outer axial through hole 60, an inner axial through hole 62, and is terminated at its distal end by a small axial groove 64. A select one of the spokes 26 includes an additional inner axial through hole 66. The central hub 24 has a circumferential channel 68, best shown in FIG. 3, which is a partial cross section view of the hub 24 and attachment member 42 taken along line A-A of FIG. 5. Hub 24 also has a radially placed recessed scalpel slot 70 that intersects the circumferential channel 68 to form a retaining suture cutting guide. Lower filleted wall 72 prevents a scalpel point from damaging the adjacent natural valve leaflet when a retaining suture 74 is cut as described below.

Figure 6:
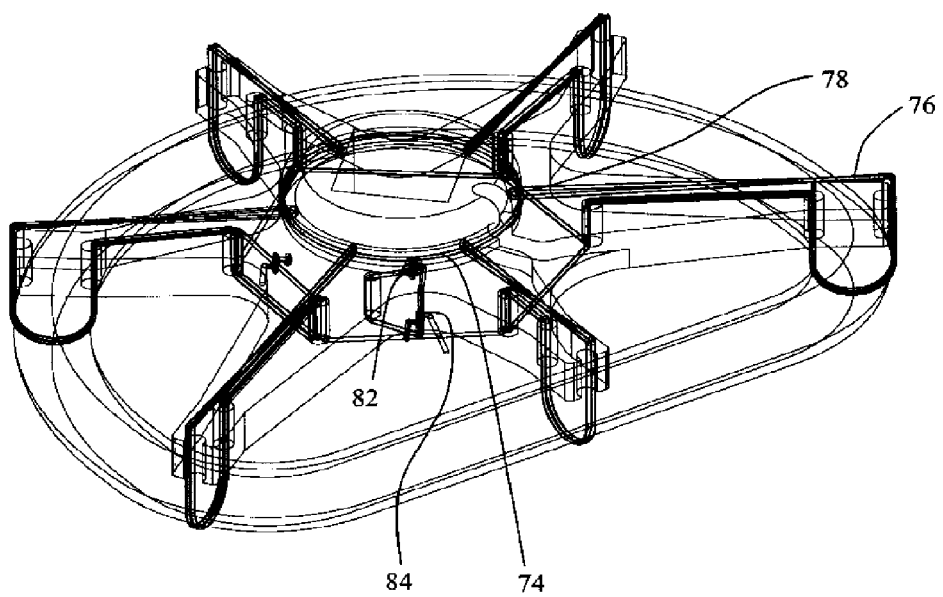
FIG. 6 is a phantom isometric view of the holder with an annuloplasty ring attached. Suture paths are shown.

As is shown in FIGS. 2 and 6, a continuous single length of ring suture material 76 (possibly with its first end overlapping hole 66) is formed into an appropriate number of loops corresponding to each spoke 26 by following the sequence described herein. The loops collectively retain the annuloplasty ring 12 to the head 14. It is important to note that other loop or tying sequences for securing an annuloplasty ring 12 to a holder head 14 with a continuous single length of ring suture 76 will be readily apparent to those skilled in the art, and are within the scope of the present invention. In addition, an annuloplasty ring 12 may be secured to the holder head 14 with more than a single length of suture material.

The securing loops may be formed by passing the ring suture 76 through the holes 60, 62 and around the ring 12 as follows. The second end of the ring suture 76 is passed upward through hole 62 in a first select spoke 26. The second end is then passed down through hole 60 of the same spoke 26 and partially wrapped around the medial, lower, and lateral quadrant sections of the annuloplasty ring 12. This end of the ring suture 76 is then passed upward along the axial groove 64 of the select spoke 26 to the upper surface 18. The second end of the ring suture 76 is then passed along the upper surface 18 of the select spoke 26 to the hub channel 68. Within the hub channel 68, the ring suture 76 will be doubled back. As is described in detail below, the ring suture 76 may be held captive at the hub with the retaining suture 74. The doubling back of the ring suture 76 causes a hairpin bend 78 such that the ring suture 76 is directed back along the upper surface 18 of the same spoke 26 returning to axial groove 64.

The second end of the ring suture material 76 is then passed down along axial groove 64 and wrapped around the annuloplasty ring 12 a second time. After thus securing the annuloplasty ring 12 with a second wrap per spoke, the ring suture 76 is passed upward through hole 60, down through hole 62, and subsequently passed in a counterclockwise or clockwise manner to an adjacent spoke 26. At the adjacent spoke 26, the loop forming process is repeated until the annuloplasty ring 12 has been secured to each spoke 26. Alternatively, the annuloplasty ring could be secured to only a select subset of all spokes.

The loop forming process is concluded when the second end of the ring suture 76 is tied to the first end at or near hole 66. The knot 80 formed between the first and second ends of the ring suture 76 is shown positioned between holes 62 of adjacent spokes 26 in FIG. 2. This knot 80 can be locate elsewhere at the discretion of the technician attaching an annuloplasty ring 12 to the head 14.

The hairpin bends 78 of the ring suture loops lie in circumferential channel 68, where they are retained by a retaining suture 74 that also lies in channel 68. The ends of the retaining suture 74 are tied in a knot 82 adjacent to hole 66. One suture knot tail end is passed downward through hole 66, is then passed upward on one side of the spoke 26, and tied to its other knot tail end. This second knot 84 may overlie knot 82 or be separate as is shown in the figures. Variations in actual suture paths and knot locations will be apparent to one skilled in the art. The method described above or alternative methods are suitable for implementation of the present invention, provided that both sutures 74, 76 are secured to the head 14 of the holder 10 and thus can not become detached from the holder 10 and thus potentially fall unnoticed into the patient's chest cavity or heart chamber.

Release of the annuloplasty ring from the holder is accomplished by using a scalpel in scalpel slot 70, hence severing the retaining suture 74, which in turn releases hairpin loops 78. The holder may then be gently removed from the ring. Hairpin loops 78 may be gently pulled from between the lower quadrants of the ring and the tissue of the annulus as part of the removal process.

The use of the holder 10 may generally be described with particular reference to FIG. 3 (a partial cross sectional view of the holder hub 24 and attachment member 42 taken along line A-A of FIG. 2), and FIG. 4. Parallel leg members 46, 44 are separated by slot 48. Stepped portions 50, 52 are terminated with chamfered flanges 54, 56. When members 46, 44 are squeezed together close to steps 50, 52, members 46, 44 bend inward sufficiently to allow flanges 54, 56 to freely enter hole 58. Handle flats 34 indicate to the surgeon the orientation of the distal flat surfaces of members 46, 44 to be compressed using artery forceps.

During implantation of the ring, double needle ended implanting sutures are first placed in the patient's heart valve annulus. The two needles of each implanting suture are then passed through the annuloplasty ring 12 approximately 3-4 mm apart, the ring being mounted onto the holder head 14 with the handle 16 attached. At this time, the ring and holder are near the patient's chest but typically outside of the surgical zone. The implantation suture is partially pulled through the ring 12. After all the needles have been passed through the ring 12, the suture bundle is grasped with a pair of forceps and the needles are cut off the sutures. The malleable stem 30 is bent as required and the annuloplasty ring 12 and holder 10 is pushed down the sutures so that the ring lies on and against the annulus. Mounting the ring 12 on the annuloplasty ring receiving surface opposite the handle 16 facilitates proper placement. The handle 16 may then be removed by squeezing together legs 44, 46 (close to steps 50, 52), thus releasing member 42 from hole 58. The handle 16 may then be withdrawn from the operative field to allow improved access to the surgeon for the tying of the implantation knots. If required, the handle may be reinserted in hole 58 after squeezing legs 44, 46 together once more. Finally, the head 14 may be released from the ring by severing retaining suture 74 at scalpel slot 70 and gently teasing loops 78 from under the annuloplasty ring at the ring/tissue interface.

Figure 7:
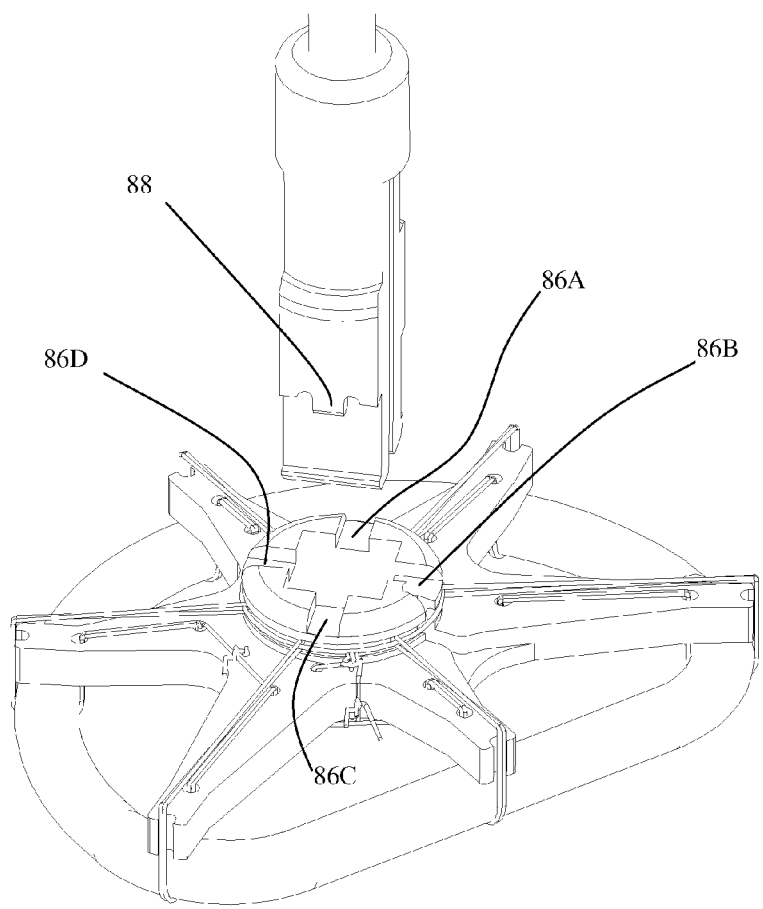
FIG. 7 is an isometric view of the holder with an annuloplasty ring attached, featuring orientation channels.

FIG. 7 is an illustration of alternative embodiment of the holder 10 similar in overall design to that illustrated in FIG. 2. In the FIG. 7 embodiment however, a series of orientation channels 86A-D are formed in the hub 24. The orientation channels 86A-D are configured to mate with an orientation tab 88 associated with the attachment member 42. The inclusion of an orientation tab 88 and orientation channels 86A-D assures that the head 14 will be mounted to the handle 16 with the proper orientation, thus guaranteeing that the annuloplasty ring receiving surface 20 is opposite the handle in use.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the invention.

The invention claimed is:

1. A method of releasing an annuloplasty ring from an annuloplasty ring holder comprising:
provided an annuloplasty ring holder;
providing an annuloplasty ring removably attached to the annuloplasty ring holder with one or more sutures, wherein the annuloplasty ring is a partial or C-shaped ring;
severing a single suture of the one or more sutures once and severing no other sutures of the one or more sutures; and
disassociating the annuloplasty ring holder from the annuloplasty ring, wherein more than one suture is attached to the annuloplasty ring holder before the step of severing only one suture and all of said sutures remain attached to the annuloplasty ring holder after disassociating the annuloplasty ring holder from the annuloplasty ring.

2. The method of releasing an annuloplasty ring from an annuloplasty ring holder of claim 1 further comprising simultaneously withdrawing the annuloplasty ring holder and the severed suture from the annuloplasty ring.

3. The method of releasing an annuloplasty ring from an annuloplasty ring holder of claim 1 wherein the annuloplasty ring is removably attached to the annuloplasty ring holder with a continuous single length of suture.

4. A method of attaching an annuloplasty ring to an annuloplasty ring holder comprising:
providing an annuloplasty ring holder;
providing an annuloplasty ring having a partial or c-shaped ring; and
attaching an annuloplasty ring to the annuloplasty ring holder with one or more sutures such that the annuloplasty ring may be released from the annuloplasty ring holder by severing once a single suture of the one or more sutures, without severing any other suture of the one or more sutures, wherein more than one suture is attached to the annuloplasty ring holder before the step of severing only one suture and all of said sutures remain attached to the annuloplasty ring holder after disassociating the annuloplasty ring holder from the annuloplasty ring.

5. The method of attaching an annuloplasty ring to an annuloplasty ring holder of claim 4 further comprising attaching each of the one or more sutures to the annuloplasty ring holder.

6. The method of attaching an annuloplasty ring to an annuloplasty ring holder of claim 5 further comprising attaching the annuloplasty ring to the annuloplasty ring holder with a continuous single length of suture.

* * * * *